United States Patent
Galt et al.

(10) Patent No.: US 6,478,775 B1
(45) Date of Patent: Nov. 12, 2002

(54) DEVICE FOR DELIVERING NON-BIODEGRADABLE BULKING COMPOSITION TO A UROLOGICAL SITE

(75) Inventors: Kenneth M. Galt, Laguna Hills, CA (US); John Wardle, San Clemente, CA (US); Thomas J. Berryman, Laguna Beach, CA (US)

(73) Assignee: Genyx Medical Inc., Aliso Viejo, CA (US)

( * ) Notice: Subject to any disclaimer, the term of this patent is extended or adjusted under 35 U.S.C. 154(b) by 2 days.

(21) Appl. No.: 09/678,431

(22) Filed: Oct. 2, 2000

(51) Int. Cl.[7] ............................................. A61M 5/178
(52) U.S. Cl. ............ 604/158; 604/164.02; 604/164.12; 604/264; 604/167.01; 604/266; 604/249
(58) Field of Search ........................... 604/158, 38, 39, 604/43, 44, 19, 517, 164.01, 162, 164.02, 164.06, 164.08, 164.09, 164.12, 165.01, 165.02, 166.01, 170.01, 170.02, 167.03, 167.06, 187, 264, 266, 267, 272–274, 157, 198, 213, 218, 235, 245, 246, 249, 22, 171, 173, 181, 192, 134, 135, 284, 523, 311, 310, 167.01; 600/29, 135; 222/151, 342; 606/213–215

(56) References Cited

U.S. PATENT DOCUMENTS

| | | | |
|---|---|---|---|
| 3,000,380 A | | 9/1961 | Doherty |
| 3,826,256 A | | 7/1974 | Smith ..................... 128/214.4 |
| 4,224,943 A | * | 9/1980 | Johnson et al. ......... 604/164.11 |
| 4,311,139 A | | 1/1982 | Smith ..................... 128/214.4 |
| 4,475,902 A | | 10/1984 | Schubert |
| 4,874,379 A | | 10/1989 | Gabran |
| 5,411,475 A | | 5/1995 | Atala et al. |
| 5,443,454 A | * | 8/1995 | Tanabe et al. ............... 604/264 |
| 5,470,316 A | * | 11/1995 | Tovey et al. ................ 604/118 |
| 5,586,553 A | * | 12/1996 | Halili et al. ................ 600/316 |
| 5,695,480 A | | 12/1997 | Evans et al. ................ 604/264 |
| 5,755,658 A | | 5/1998 | Wallace et al. ............... 600/30 |
| 5,785,642 A | | 7/1998 | Wallace et al. ............... 600/30 |
| 5,813,411 A | | 9/1998 | Van Bladel et al. |
| 5,958,444 A | | 9/1999 | Wallace et al. ............. 424/430 |
| 5,976,110 A | * | 11/1999 | Greengrass et al. ........ 604/158 |
| 6,071,230 A | | 6/2000 | Henalla |
| 6,146,373 A | * | 11/2000 | Cragg et al. .................. 604/19 |
| 6,234,955 B1 | * | 5/2001 | Silverman et al. ............ 600/29 |
| 6,254,586 B1 | * | 7/2001 | Mann et al. ................. 206/365 |
| 6,258,055 B1 | * | 7/2001 | McCrory et al. ............. 604/57 |
| 6,336,915 B1 | * | 1/2002 | Scarfone et al. ............ 604/171 |

FOREIGN PATENT DOCUMENTS

| | | |
|---|---|---|
| EP | 818208 A2 | 1/1998 |
| WO | WO 97/17105 | 5/1997 |

OTHER PUBLICATIONS

Rodney A. Appell, M.D. "Periurethral Injection Therapy", 1109–1120.

Di Segni, Riccardo, et al., "*Vascular Embolotherapy,*" Interventional Radiology, 3rd Edition, pp. 29–103.

Vedantham, Suresh, M.D., et al., "*Uterine artery embolization: An underused method of controlling pelvic hemorrhage,*" American Journal Obstetrics and Gynecology, Apr. 1997, pp. 938–948.

* cited by examiner

Primary Examiner—Brian L. Casler
Assistant Examiner—Cris Rodriguez
(74) Attorney, Agent, or Firm—Burns, Doane, Swecker & Mathis L.L.P.

(57) ABSTRACT

A device for delivery of a biocompatible polymer composition for treatment of urinary incontinence provides for delivery of biocompatible polymer material and a solidification agent through two lumens. The delivery device provides better control of the precipitation of the polymer in the periurethral tissue and detachment of the precipitated mass from the delivery device. The medical device includes a needle having a lumen and an inner cannula positioned within the needle lumen and movable longitudinally in the needle lumen from an extended position to a withdrawn position to sheer or cut the delivered mass of polymer material away from the needle tip.

25 Claims, 7 Drawing Sheets

DEVICE FOR DELIVERING NON-BIODEGRADABLE BULKING COMPOSITION TO A UROLOGICAL SITE

BACKGROUND OF THE INVENTION

1. Field of the Invention

The invention relates to a medical device, and more particularly, the invention relates to a medical device for delivering a non-biodegradable bulking composition to a urological site to treat urinary incontinence.

2. Brief Description of the Related Art

Urinary incontinence is an extremely common problem especially in women. In particular, many women suffer from stress incontinence. In this condition, the pelvic-floor tissues which support the urethra are weakened by, for example, childbirth or obesity. As a result, when pressure is exerted on these tissues by coughing, lifting, etc., urine is involuntarily discharged from the bladder through the urethra.

The initial treatment for stress incontinence typically consists of exercises to strengthen the pelvic-floor muscles. If these exercise are ineffective, open surgical repair of the bladder neck is often attempted. However, such surgical repair procedures are not successful for all patients. Moreover, there are always certain risks associated with open surgical procedures, such as infection, risks of anesthesia, etc.

As an alternative to surgical repair, urinary incontinence has been treated by periurethral injection therapy, in which a substance is injected into the tissue surrounding the urethra, i.e., the periurethral tissue, to add bulk to this tissue. The aim of this treatment is to restore the proximal urethra to its proper normally closed condition and to keep it closed during coughing, straining, or exercise. The injected substance compresses the urethra at the level of the bladder neck thus impeding the involuntary flow of urine from the bladder.

Many injectable substances have been tried for this purpose with varying results. For example, in the first half of the twentieth century sclerosing solutions, such as sodium morrhuate or cod liver oil were injected into the anterior vaginal wall. An inflammatory response developed with secondary scarring which resulted in compression of the incompetent urethra. Although this material was successful in curing incontinence in some patients, complications included pulmonary infarction and cardiac arrest. Similarly, paraffin and other sclerosing solutions have been tried with poor results.

More recently, polytetrafluoroethylene particles (TEFLON™, POLYTEF™) have been used as an injectable material for the correction of urinary incontinence with a success rate of from 30% to 86% in some studies. However, these particles have subsequently been demonstrated to generate foreign body granulomas and to migrate to distant organs, such as the lungs, liver, spleen and brain. Accordingly, the use of polytetrafluoroethylene particles is currently disfavored.

Another injectable material that has been used recently for the treatment of urinary incontinence is glutaraldehyde cross-linked bovine dermal collagen. However, a major problem associated with the use of collagen materials is the tendency of the implant to decrease in volume over time thereby necessitating retreatment. In addition, collagen has been associated with adverse immune responses and allergic reactions to bovine dermal collagen have been described.

Various other injectable substances have been reported or proposed as implant materials for the treatment of bladder conditions, such as vesicoureteral reflux. These substances include polyvinyl alcohol foam, glass particles, a chondrocyte-alginate suspension, and a detachable silicone balloon.

In addition to the various problems associated with many of the substances used to treat urinary incontinence, the methods currently employed for delivering injectable materials to the periurethral tissue have certain disadvantages. In particular, the amount of material necessary to compress the urethra must typically be estimated by observing the compression of the urethra wall using a cystoscope or endoscope. If an insufficient amount of material is injected in the first procedure, top-up injections administered in subsequent procedures may be necessary. In addition, the materials which are delivered may be absorbed by the body over time requiring retreatment. Other materials which are used are hydrateable and swell within the body causing difficulty in predicting a final size of the injected material.

U.S. Pat. Nos. 5,755,658 and 5,785,642, which are incorporated herein by reference in their entirety, describe methods of delivering a composition comprising a biocompatible polymer and a biocompatible solvent to the periurethral tissue. The biocompatible solvent is miscible or soluble in the fluid of the periurethral tissue and, upon contact with these fluids, the biocompatible solvent quickly diffuses away. Upon diffusion of the solvent, the biocompatible polymer precipitates to form an occlusion in the periurethral tissue which compresses the urethra thereby preventing or reducing the involuntary leakage of urine from the bladder.

However, there are certain drawbacks to the use of conventional delivery systems with the biocompatible polymer composition. In particular, the biocompatible polymer composition is injected into the periurethral tissue as a flowable composition which may not solidify instantaneously. Accordingly, it would be desirable to provide faster solidification and better control of the delivery of the biocompatible polymer composition. It would also be desirable to provide these advantages for other compositions which are delivered as two liquids to form a solid.

SUMMARY OF THE INVENTION

The present invention relates to a medical device for delivery of a biocompatible polymer composition to the periurethral tissue to treat urinary incontinence.

In accordance with one aspect of the present invention, a medical device includes a needle and an inner cannula positioned within the needle lumen and movable longitudinally in the needle lumen. The inner cannula has a lumen for delivering a first fluid and the needle has a lumen for delivering a second fluid. The inner cannula has a cannula tip configured to detach a mass from the needle when the inner cannula is moved from an extended position at which the cannula tip extends from a distal end of the needle to a withdrawn position at which the cannula tip is within the needle lumen.

In accordance with an additional aspect of the present invention, a medical device includes an inner cannula, an outer cannula coaxially surrounding the inner cannula, an injection hub connected to the inner and outer cannulas, and a movable piston within the injection hub. The piston is connected to the inner cannula for moving the inner cannula within the outer cannula, wherein the movable piston is actuated by a delivered fluid which is delivered through the inner or outer cannula.

In accordance with a further aspect of the invention, a device for delivering non-biodegradable bulking composition to a urological site includes a needle, an inner cannula longitudinally movable within the needle, the inner cannula having a distal end with a trumpet shaped tip, and an injection hub connected to the needle and inner cannula for delivery of first and second fluids through the needle and inner cannula.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

The invention involves a device for treatment of urinary incontinence in mammals by delivering sufficient amounts of a composition comprising a biocompatible polymer and a biocompatible solvent to the periurethral tissue under conditions such that a polymer precipitate forms in situ in the periurethral tissue. This polymer precipitate compresses the urethral opening thereby affording increased outlet resistance and reducing urinary incontinence in the mammal.

A device for delivery of the biocompatible polymer composition according to the present invention provides for delivery of a solidification agent in addition to the polymer material. The solidification agent is delivered with the polymer material to provide better control of the precipitation of the polymer in the periurethral tissue. Without the delivery of the solidification agent, the polymer material may solidify slowly which may allow the polymer to pass backward into the needle entry channel. The polymer may also adhere itself to the needle tip making needle withdrawal difficult.

When the polymer material is adhered to the needle tip, upon withdrawal of the needle, some of the polymer material may be dragged out of the implant site along with the needle. The device according to the present invention provides a plurality of needle tips for detachment of a solidified or partially solidified polymer mass from the tip of the needle. The needle tips detach the solidified mass by moving an inner cannula with respect to an outer cannula to shear or cut the mass away from the needle tip.

As shown in the embodiment of FIGS. 1–4, a delivery needle 10 includes an angled piercing tip 12 and an inner cannula 14. A distal end of the inner cannula 14 has a trumpet shaped tip 16. The inner cannula 14 is movable from the extended position illustrated in FIGS. 1 and 2 to a withdrawn position illustrated in FIGS. 3 and 4.

Figures 1, 2, 3, 4:
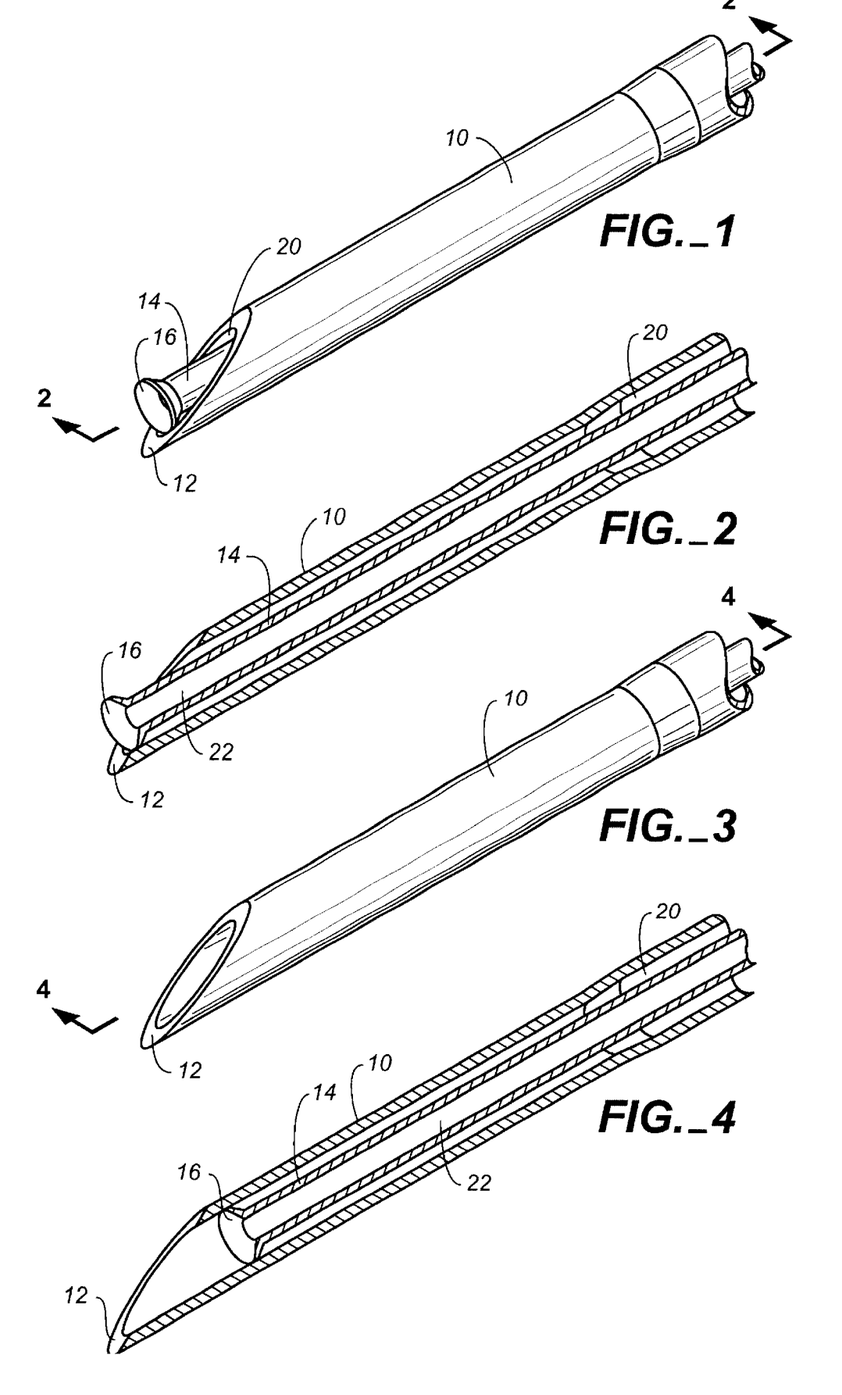
FIG. 1 is a perspective view of one embodiment of a needle tip according to the present invention with an inner cannula in an extended position for delivery of the biocompatible polymer composition.
FIG. 2 is a cross section taken along line 2—2 of FIG. 1.
FIG. 3 is a perspective view of the needle tip of FIG. 1 with the inner cannula in a withdrawn position for detachment of the biocompatible polymer mass.
FIG. 4 is a cross section taken along line 4—4 of FIG. 3.

In use, once the needle 10 is placed at an injection site in the periurethral tissue, the inner cannula 14 is moved to the extended position as shown in FIG. 1 for injection of the polymer material through an outer lumen 20 between the inner surface of the needle 10 and the outer surface of the inner cannula 14. Once the polymer injection is completed, the inner cannula 14 is withdrawn as illustrated in FIGS. 3 and 4. During withdrawal of the inner cannula 14, an edge of the trumpet shaped tip 16 cuts or shears the polymer material against an inner surface of the needle tip 12 detaching the precipitated solid mass of polymer material from the needle tip and allowing the needle tip to be easily withdrawn from the injection site. A solidification agent, such as saline, is injected through the inner lumen 22 of the inner cannula 14 after delivery of the polymer material is complete. The solidification agent both solidifies the polymer material and aids in separating the polymer from the needle. The solidification agent may also be delivered before or during delivery of the polymer material.

Figure 5:
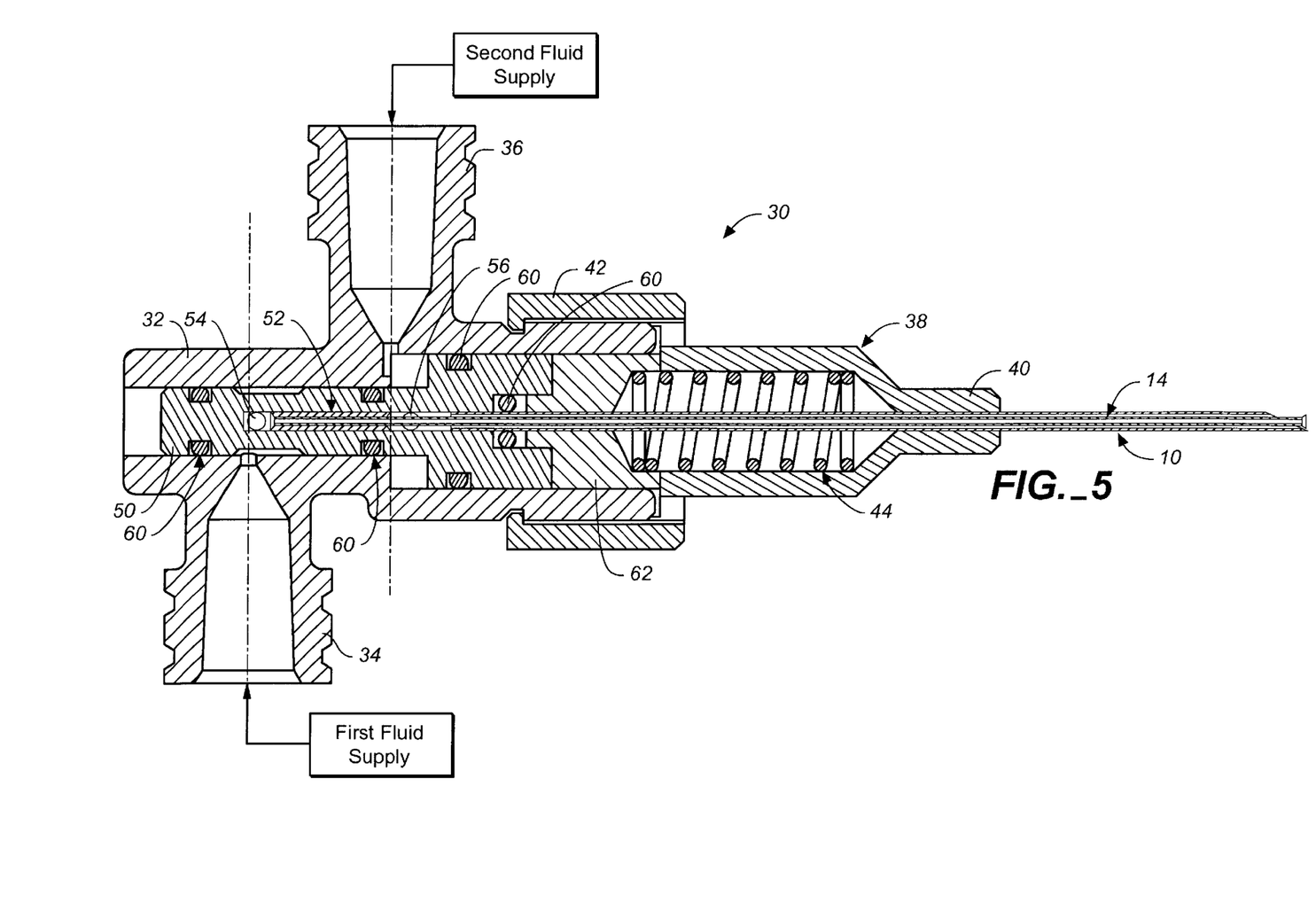
FIG. 5 is a side cross sectional view of an injection device according to the present invention.

FIG. 5 illustrates an injection hub 30 of the present invention which is provided for delivery of fluids to the outer and inner lumens 20, 22 of the needle 10 and inner cannula 14 (shown in FIGS. 1–4). The injection hub 30 includes a body 32 having first and second fluid injection ports 34, 36 for delivery of first and second fluids. The needle 10 is fixed to the body 32 by a distal sleeve 38. The distal sleeve 38 has a first end 40 which is fixed to the needle 10 and a second end 42 which is secured to the injection hub body 32. Contained within the distal sleeve 38 is a compression spring 44 for providing a proximal bias to a piston 50.

The piston 50 is fixed to the inner cannula 14 by a sleeve 52. Longitudinal motion of the piston 50 inside the body 32 provides motion of the inner cannula 14 with respect to the needle 10. The solidification agent is delivered through the first injection port 34 and through a first opening 54 in the piston 50 into the inner lumen 22 of the inner cannula 14. The polymer material is delivered from the second injection port 36 and through a second opening 56 in the piston 50 to the outer lumen 20 between the needle 10 and the inner cannula 14.

In the position illustrated in FIG. 5, the piston 50 is biased forward by fluid pressure on the piston created by delivery of the polymer material through the second fluid injection port 36. The injection pressure of the polymer material advances the piston 50 which in turn advances the trumpet shaped tip 16 to the extended position. Stopping the injection of the polymer material into the second fluid injection port 36 relieves the forward pressure on the piston 50. With the forward pressure removed, the compression spring 44 returns the piston 50 and the trumpet shaped tip 16 of the inner cannula 14 to a retracted position.

The withdrawal of the trumpet shaped tip 16 into the needle 10 detaches and separates the polymer material from the needle tip 12. The solidification agent is preferably injected through the inner lumen 22 after withdrawal of the trumpet shaped tip 16. The solidification agent injection insures that the polymer material is precipitated to a solid at an area adjacent the needle entry channel before the needle assembly is withdrawn from the injection site to allow the polymer material to be detached from the needle tip and prevent the polymer material from passing into the needle entry channel once the needle has been withdrawn. The severing of the polymer material below the tissue surface prevents infection and/or non-healing of the tissue surface which may occur when the polymer material extends to or through the tissue surface.

A plurality of O-rings 60 are provided in the injection hub 30 between the body 32 and the piston 50. The O-rings contain and isolate the fluids which are injected through the first and second injection ports 34, 36. An O-ring retainer plate 62 is also provided which retains the distal most O-ring in place inside the piston 50.

Figures 6, 7, 8, 9:
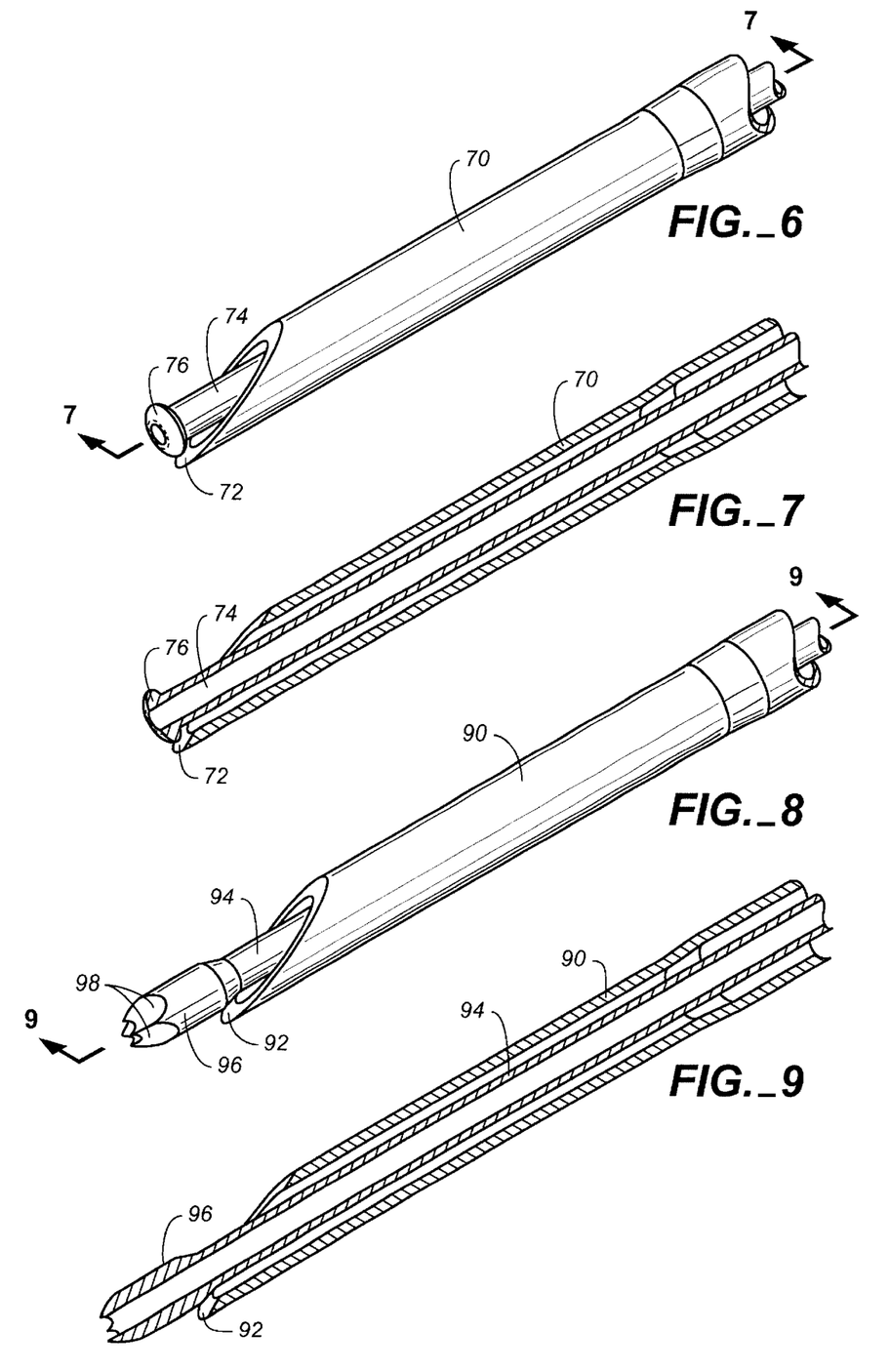
FIG. 6 is a perspective view of a second embodiment of a needle tip according to the present invention with the inner cannula in an extended position.
FIG. 7 is a cross section taken along line 7—7 of FIG. 6.
FIG. 8 is a perspective view of a third embodiment of a needle tip according to the present invention with the inner cannula in an extended position.
FIG. 9 is a cross section taken along line 9—9 of FIG. 8.

FIGS. 6 and 7 illustrate an alternative embodiment of a needle 70 having an angled needle tip 72 and an inner cannula 74 with a disk shaped tip 76. The disk shaped tip 76 has an outer diameter which larger than an outer diameter of a remainder of the inner cannula 74 and is less than or equal to the inner diameter of the needle 70. The disk shaped tip 76 has blunt rounded edges. When the inner cannula 74 is moved from the extended position of FIGS. 6 and 7 to a retracted position, the disk shaped tip 76 separates the polymer mass from the needle tip 72 by cutting or shearing of the polymer mass between the disk shaped tip 76 and the inner surface of the needle tip 72. The disk shaped tip 76 provides the advantages of the trumpet shaped embodiment of FIGS. 1–4 with the additional advantage of preventing secondary cutting or piercing of soft tissue when the disk shaped tip 76 is extended from the end of the needle 70.

FIGS. 8 and 9 illustrate an alternative embodiment of a needle 90 having a tip 92 and a movable inner cannula 94 with a trocar tip 96. The trocar tip 96 has a plurality of bevels 98 forming a sharp cutting tip which can be used to cut through firm tissue which would prevent the trocar tip 96 from being advanced out of the needle 90. The trocar tip 96 has an outer diameter which larger than an outer diameter of a remainder of the inner cannula 94 and is less than or equal to the inner diameter of the needle 90. When the inner cannula 94 is moved from the extended position of FIGS. 8 and 9 to a retracted position, the trocar tip 96 separates the polymer mass from the needle tip 72 by cutting or shearing of the polymer mass between the trocar tip and the interior of the needle tip 92.

Figure 10:
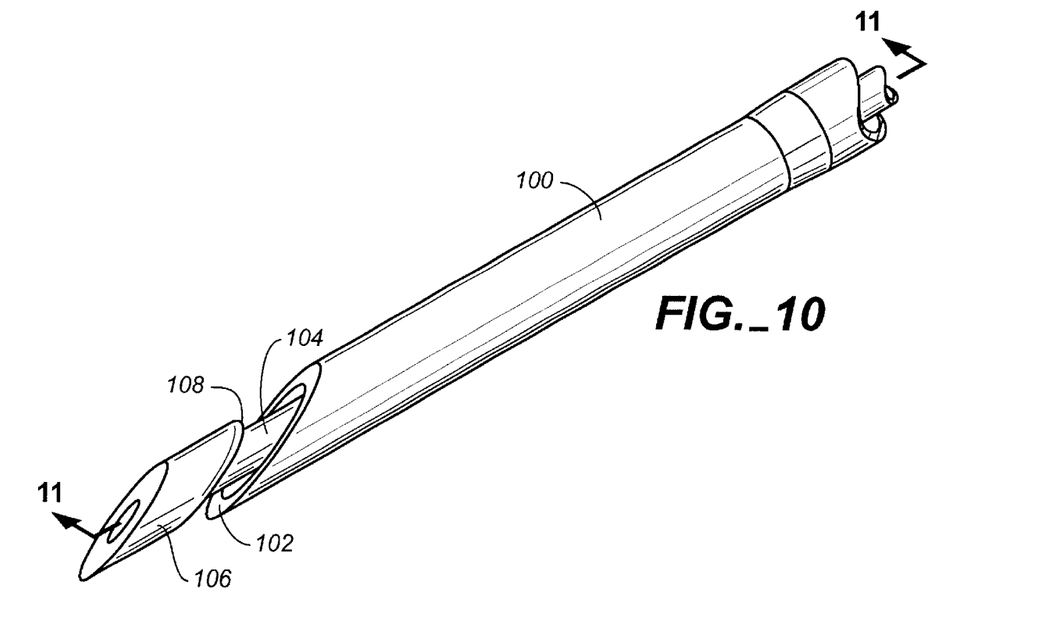
FIG. 10 is a perspective view of a fourth embodiment of a needle tip according to the present invention with the inner cannula in an extended position.
Figure 11:
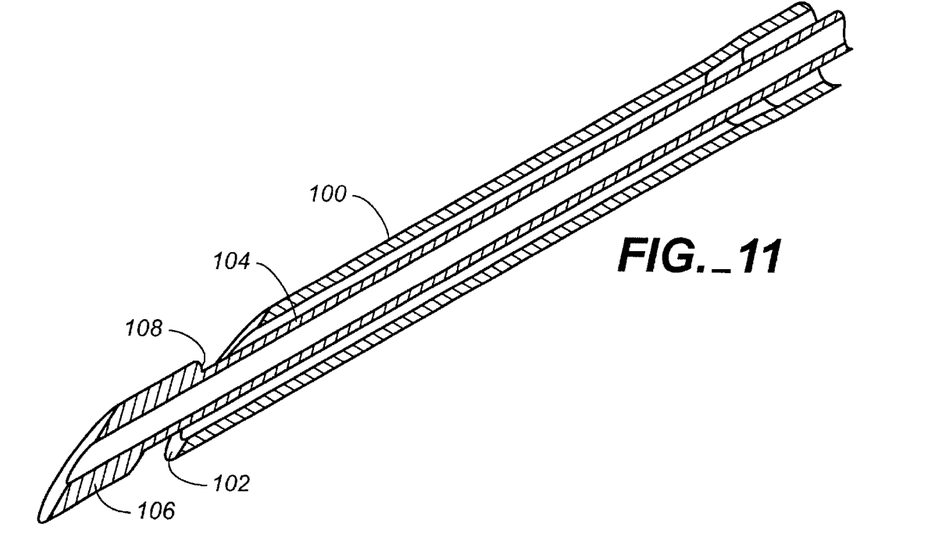
FIG. 11 is a cross section taken along line 11—11 of FIG. 10.

FIGS. 10 and 11 illustrate another embodiment of a needle 100 having an angled needle tip 102 and a movable inner cannula 104 with an enlarged angled cannula tip 106. As in the embodiment of FIGS. 8 and 9, the angled cannula tip 106 provides a sharp cutting tip which can be used to cut through firm tissue which would prevent the inner cannula 104 from being advanced from the needle 90. The angled cannula tip 106 has an outer diameter which is larger than an outer diameter of a remainder of the inner cannula 104 and is less than or equal to the inner diameter of the needle 100. A rounded shoulder 108 is provided on the inner cannula 104 proximal of the distal end of the cannula. When the inner cannula 104 is withdrawn into the needle 100, the shoulder 108 traps and shears the polymer mass between the shoulder and the needle tip 102 separating the polymer mass from the needle tip 102.

Figure 12:
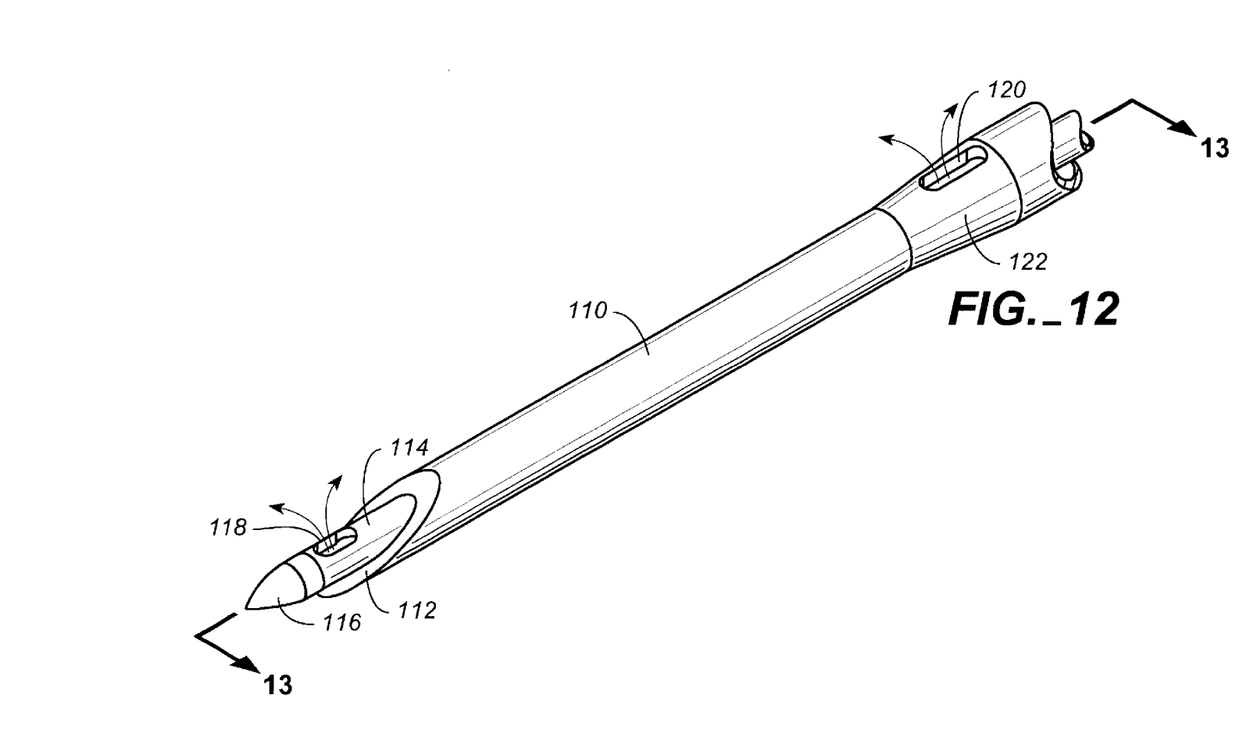
FIG. 12 is a perspective view of a fifth embodiment of a needle tip according to the present invention with the inner cannula in an extended position.
Figure 13:
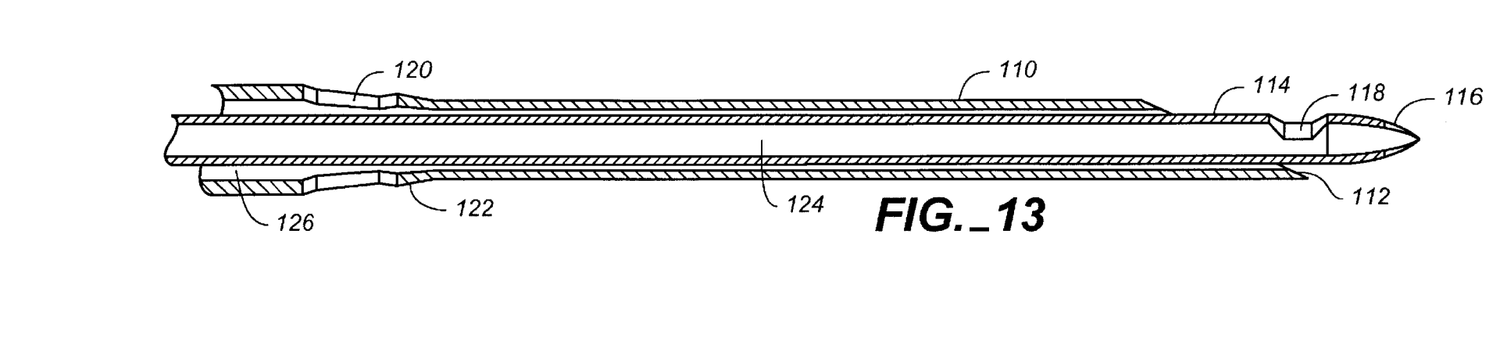
FIG. 13 is a side cross sectional view of the embodiment of FIG. 12 taken long line 13—13.

FIGS. 12 and 13 illustrate an embodiment of a needle 110 having an angled needle tip 112 and an inner cannula 114. The inner cannula 114 has a pointed tip 116 and a side opening 118 at a location just proximal the pointed tip. The pointed cannula tip 116 may be either blunt or sharp. The needle 110 has a side opening 120 proximal of the needle tip 112 at the location of a tapered portion 122 of the needle. In operation, a first fluid is delivered through a lumen 124 of the cannula 114 and out of the cannula side opening 118. A second fluid is delivered through an annular lumen 126 between the needle 110 and the inner cannula 114. According to one embodiment, the first fluid is a bulking agent including a polymer and a solvent and the second fluid is a solidification agent. For treatment of urinary incontinence, the polymer material is preferably delivered through the inner cannula 114 and the solidification agent is delivered through the side opening 120 of the needle 110. The location of the side opening 120 of the needle may be arranged to be at or near the site where the needle 110 enters the tissue. This will assure complete solidification of the polymer material at the needle entry point and will prevent polymer material from extending out of the tissue and preventing healing or causing infection.

In the embodiment of FIGS. 12 and 13, the inner cannula 114 fits within a portion of the needle 110 distal of the taper 122 with a fit which substantially prevents fluid from passing between the needle and the inner cannula causing the fluid passing through the annular lumen 126 to exit through the opening 120 in the side wall of the needle. When the inner cannula 114 is retracted into the needle 110, the polymer mass is cut or sheared between the needle tip 112 and the edges of the cannula side opening 118.

Figure 14:
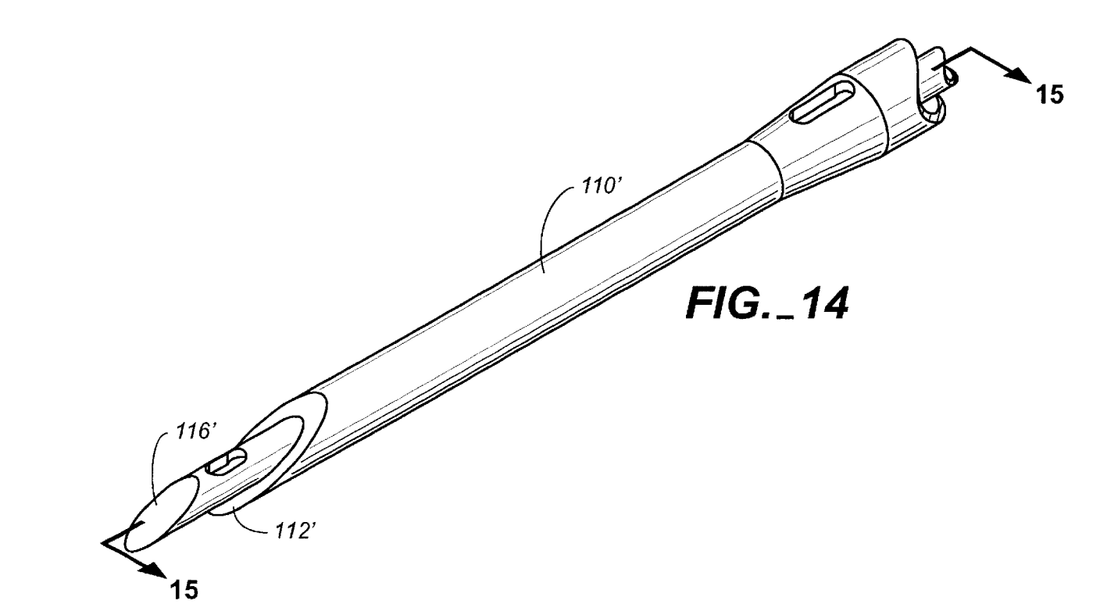
FIG. 14 is a perspective view of a sixth embodiment of a needle tip according to the present invention with the inner cannula in an extended position.
Figure 15:
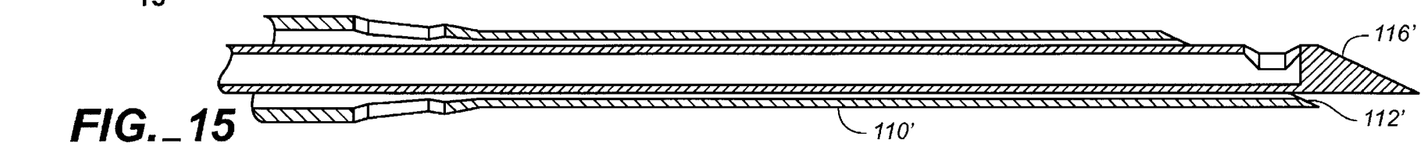
FIG. 15 is a side cross sectional view of the embodiment of FIG. 14 taken along line 15—15.
Figure 16:
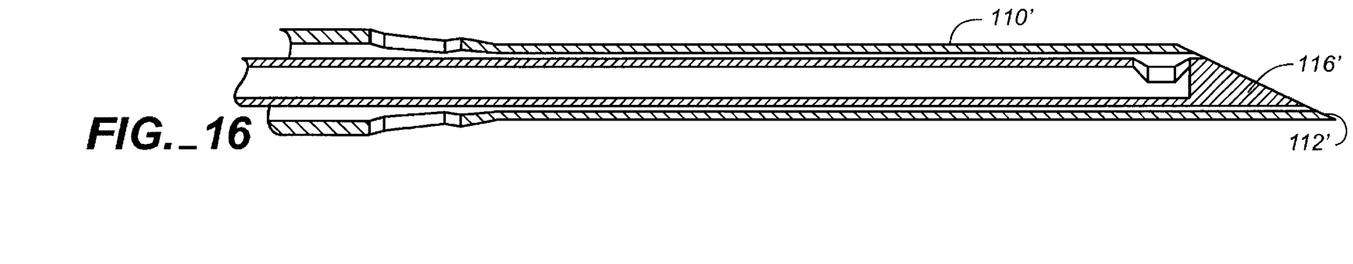
FIG. 16 is a side cross sectional view of the embodiment of FIG. 15 with the inner cannula in a withdrawn position for detachment of the solid mass from the needle tip.

FIGS. 14–16 illustrate an embodiment of a needle 110' similar to that of FIGS. 12 and 13 in which the needle tip 112' and cannula tip 116' are both formed at the same angle. The point of the cannula tip 116' may be used for penetrating tissue as the inner cannula 114' is advanced out of the needle 110'. FIG. 16 illustrates the inner cannula 114' in the retracted needle inserting position. As can be seen in FIG. 16, during insertion of the needle tip 112' the inner cannula 114' can be positioned to prevent coring of tissue with the needle.

Figure 17:
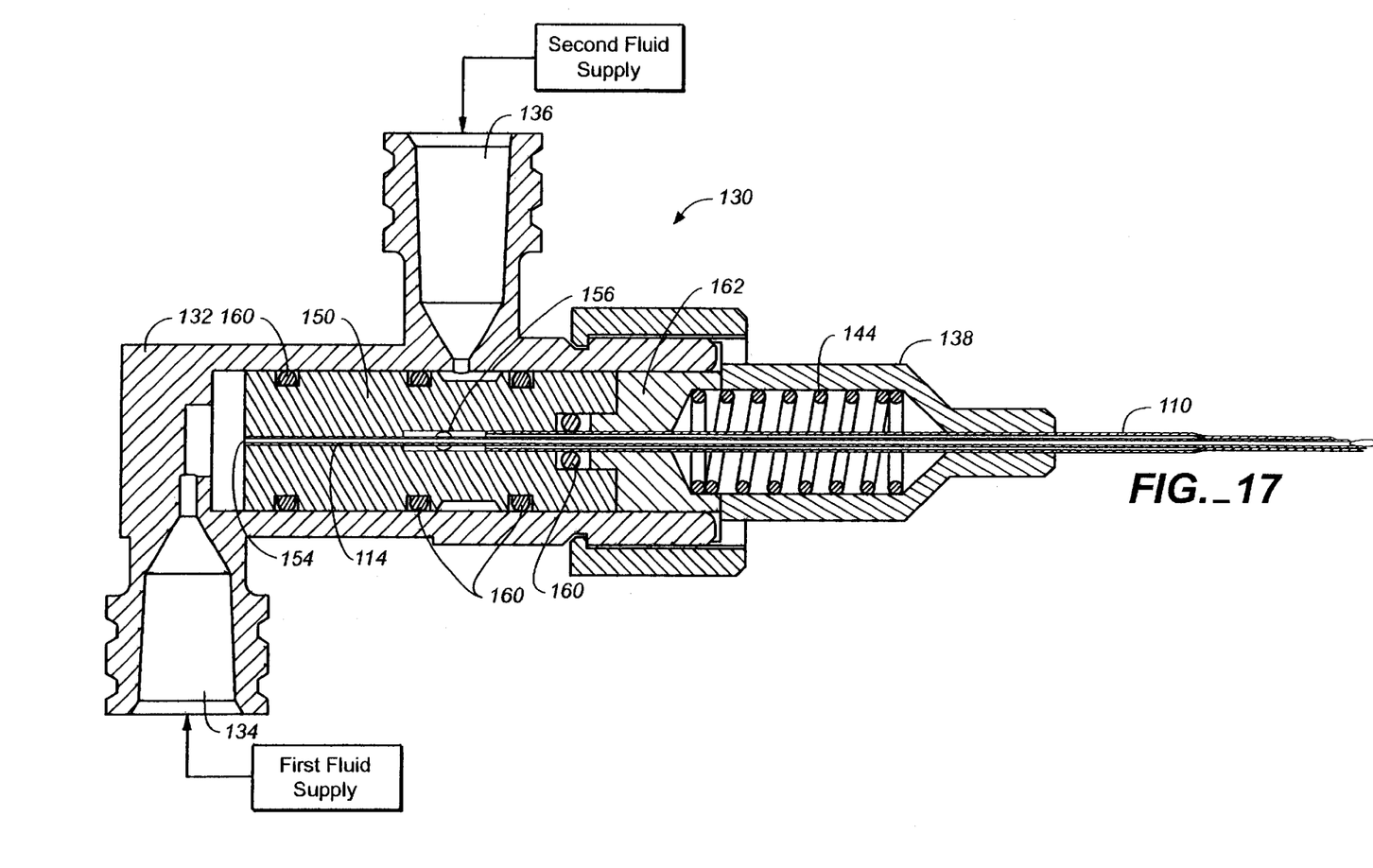
FIG. 17 is a side cross sectional view of an alternative embodiment of the injection device.

FIG. 17 illustrates an alternative embodiment of an injection hub 130. The injection hub 130 is particularly designed for use with the needles 110, 110' of FIGS. 12–16 in which the polymer material is delivered through the center lumen 124 of the inner cannula 114 and the solidification agent is delivered through the annular lumen 126 between the needle and the inner cannula. The injection hub 130 includes a body 132 having a first fluid injection port 134 for injection of the polymer material and a second fluid injection port 136 for injection of the solidification agent. The needle 110 is fixed to the body 132 by a distal sleeve 138. Contained within the distal sleeve 138 is a compression spring 144 for providing a proximal bias to a piston 150.

The piston 150 is fixed to the inner cannula 114. Longitudinal motion of the piston 150 inside the body 132 provides motion of the inner cannula 114 with respect to the needle 110. The polymer material is delivered through the first injection port 134 and through a central opening 154 in the piston 150 into the inner lumen 124 of the inner cannula 114. The solidification agent is delivered from the second injection port 136 and through a side opening 156 in the piston 150 to the outer annular lumen 126 between the needle 110 and the inner cannula 114.

In the position illustrated in FIG. 17, the piston 150 is biased forward by fluid pressure on the piston created by delivery of the polymer material through the first fluid injection port 134. The injection pressure of the polymer material advances the piston 150 which in turn advances the cannula 114 to the extended position. Stopping the injection of the polymer material into the first fluid injection port 134 relieves the forward pressure on the piston 150. With the forward pressure removed, the compression spring 144 returns the piston 150 and the inner cannula 114 to a retracted position detaching the polymer material from the needle tip 112.

The solidification agent may be injected through the outer annular lumen 126 before, during, and/or after delivery of the polymer material. In a preferred embodiment the solidification agent is delivered after the polymer material. The solidification agent injection insures that the polymer material is precipitated to a solid at an area substantially adjacent a site where the needle 110 enters the tissue.

A plurality of O-rings 160 are provided in the injection hub 130 between the body 132 and the piston 150. The O-rings contain and isolate the fluids which are injected through the first and second injection ports 134, 136. An O-ring retainer plate 162 is also provided which retains the distal most O-ring in place inside the piston 150.

The device according to the present invention is preferably designed for use with a cytoscope or other endoscope. The length of the needle 10 will vary depending on the application, however, the needle length is preferably about 15 to about 225 cm.

The polymeric compositions used in this invention are preferably nonbiodegradable and, accordingly, do not substantially decrease in volume over time. Moreover, the injection process provides for a coherent mass, not particulates, which mass is nonmigratory.

The polymeric compositions may optionally include one or more contrast agent. The contrast agent permits monitoring of the injection by conventional methods while it is taking place to ensure that it is being carried out properly. The contrast agent also allows monitoring post-injection by conventional methods to ensure correct placement of the mass months or even years after injection. Conventional monitoring methods include, by way of example, fluoroscopy, ultrasound, and in some cases visual detection.

Although the present invention has been described for use in delivering a bio-compatible polymer which solidifies in periurethral tissue to provide treatment of urinary incontinence, the injection device of the present invention may also be used for treatment of other conditions such as urinary reflux. A method of treating urinary reflux is described in U.S. Pat. No. 5,958,444 which is incorporated herein by reference in its entirety. The injection device of the present invention may also be used for delivery of other fluids. For example, the system may be used for delivery of a two-agent combination where one agent is a catalyst that enables solidification of the other agent (i.e., epoxy).

While the invention has been described in detail with reference to the preferred embodiments thereof, it will be apparent to one skilled in the art that various changes and modifications can be made and equivalents employed, without departing from the present invention.

What is claimed is:

1. A medical device comprising:

a needle having a lumen; and an inner cannula positioned within the needle lumen and movable longitudinally in the needle lumen, the inner cannula having a lumen for delivering a first fluid to the patient and the needle lumen arranged for delivering a second fluid to a patient, the inner cannula having a cannula tip configured to detach a mass from the needle when the inner cannula is moved from an extended position at which the cannula tip extends from a distal end of the needle to a withdrawn position at which the cannula tip is within the needle lumen, wherein the inner cannula is movable by fluid pressure.

2. The medical device of claim 1, wherein the cannula tip is a disk shaped tip.

3. The medical device of claim 1, wherein the cannula tip is an angled needle shaped tip.

4. The medical device of claim 1, wherein the cannula tip includes a side opening for delivering the first fluid to the patient and the side opening is configured to cut or shear a mass away from the distal end of the needle when the cannula is moved from the extended position to the withdrawn position.

5. The medical device of claim 1, further comprising an injection hub connected to the needle and the inner cannula and configured to deliver the first fluid though the lumen of the inner cannula and the second fluid between an inner surface of the needle and an outer surface of the inner cannula.

6. The medical device of claim 1, further comprising a supply of injectable material for controlling urinary incontinence connected to the needle.

7. The medical device of claim 6, further comprising a supply of a secondary fluid connected to the inner cannula.

8. A medical device comprising:

a needle having a lumen; and an inner cannula positioned within the needle lumen and movable longitudinally in the needle lumen, the inner cannula having a lumen for delivering a first fluid to the patient and the needle lumen arranged for delivering a second fluid to a patient, the inner cannula having a cannula tip configured to detach a mass from the needle when the inner cannula is moved from an extended position at which the cannula tip extends from a distal end of the needle to a withdrawn position at which the cannula tip is within the needle lumen, wherein the cannula tip is a trumpet shaped tip.

9. The medical device of claim 8, wherein the trumpet shaped tip of the inner cannula is configured to cut or shear a mass away from the distal end of the needle when the cannula is moved from the extended position to the withdrawn position.

10. A medical device comprising:

a needle having a lumen; and an inner cannula positioned within the needle lumen and movable longitudinally in the needle lumen, the inner cannula having a lumen for delivering a first fluid to the patient and the needle lumen arranged for delivering a second fluid to a patient, the inner cannula having a cannula tip configured to detach a mass from the needle when the inner cannula is moved from an extended position at which the cannula tip extends from a distal end of the needle to a withdrawn position at which the cannula tip is within the needle lumen, wherein the cannula tip has a diameter larger than a remainder of the inner cannula.

11. A medical device comprising:

a needle having a lumen;

an inner cannula positioned within the needle lumen and movable longitudinally in the needle lumen, the inner cannula having a lumen for delivering a first fluid to the patient and the needle lumen arranged for delivering a second fluid to a patient, the inner cannula having a cannula tip configured to detach a mass from the needle when the inner cannula is moved from an extended position at which the cannula tip extends from a distal end of the needle to a withdrawn position at which the cannula tip is within the needle lumen; and an injection hub connected to the needle and the inner cannula and configured to deliver the first fluid though the lumen of the inner cannula and the second fluid between an inner surface of the needle and an outer surface of the inner cannula, wherein the injection hub includes a fluid actuated piston connected to the inner cannula.

12. The medical device of claim 11, wherein the injection of the second fluid into the injection hub actuates the piston.

13. The medical device of claim 11, wherein the injection of the first fluid into the injection hub activates the piston.

14. A medical device comprising:

a needle having a lumen;

an inner cannula positioned within the needle lumen and movable longitudinally in the needle lumen, the inner cannula having a lumen for delivering a first fluid to the patient and the needle lumen arranged for delivering a second fluid to a patient, the inner cannula having a cannula tip configured to detach a mass from the needle when the inner cannula is moved from an extended position at which the cannula tip extends from a distal end of the needle to a withdrawn position at which the cannula tip is within the needle lumen; and an injection hub having a movable member connected to the inner cannula, such that injection of one of the first and second fluids into the hub moves the movable member and the inner cannula.

15. A fluid delivery device comprising:

an inner cannula;

an outer cannula coaxially surrounding the inner cannula;

an injection hub connected to the inner and outer cannulas; and a movable piston within the injection hub, the piston connected to the inner cannula for moving the inner cannula within the outer cannula, wherein the movable piston is actuated by a delivered fluid which is delivered through the inner or outer cannula.

16. The fluid delivery device of claim 15, wherein the movable piston has a spring for biasing the piston to a first position in which the inner cannula is withdrawn.

17. The fluid delivery device of claim 16, wherein the movable piston has a second position in which the inner cannula is extended and fluid pressure of the delivered fluid moves the piston from the first position to the second position.

18. A device for delivering non-biodegradable bulking composition to a urological site, the device comprising:

a needle;

an inner cannula longitudinally movable within the needle, the inner cannula having a distal end with an enlarged tip configured to detach a mass from the needle when the enlarged tip is moved into the needle; and an injection hub connected to the needle and inner cannula for delivery of first and second fluids through the needle and inner cannula.

19. The device of claim 18, further comprising a supply of injectable material for controlling urinary incontinence connected to the needle.

20. The device of claim 19, further comprising a supply of a solidification agent connected to the inner cannula.

21. The medical device of claim 18, wherein the enlarged tip of the inner cannula has an outer diameter larger than an outer diameter of a remainder of the cannula.

22. The medical device of claim 18, wherein the enlarged tip of the inner cannula is configured to separate a delivered mass from the distal end of the needle when the cannula is moved from an extended position to a withdrawn position by cutting or shearing.

23. The medical device of claim 18, wherein the inner cannula is movable by fluid pressure.

24. The medical device of claim 18, wherein the enlarged tip is a trumpet shaped tip.

25. The medical device of claim 18, wherein the enlarged tip is a disk shaped tip.

* * * * *